United States Patent [19]

Shuman et al.

[11] 3,948,886

[45] Apr. 6, 1976

[54] 6-SUBSTITUTED PURINE 3',5'-CYCLIC NUCLEOTIDES

[75] Inventors: Dennis A. Shuman, Mission Viejo; Rich B. Meyer, Jr., Laguna Beach; Roland K. Robins, Santa Ana, all of Calif.

[73] Assignee: ICN Pharmaceuticals, Inc., Irvine, Calif.

[22] Filed: June 8, 1973

[21] Appl. No.: 368,323

Related U.S. Application Data

[63] Continuation-in-part of Ser. No. 234,371, March 13, 1972, abandoned.

[52] U.S. Cl. ............................ 260/211.5 R; 424/180
[51] Int. Cl.² ......................................... C07H 19/20
[58] Field of Search ............................. 260/211.5 R

[56] References Cited
UNITED STATES PATENTS

| | | | |
|---|---|---|---|
| 2,993,039 | 7/1961 | Schroeder | 260/211.5 R |
| 3,300,479 | 1/1967 | Hanze | 260/211.5 R |
| 3,535,207 | 10/1970 | Shiro et al. | 260/211.5 R |
| 3,712,885 | 1/1973 | Weimann et al. | 260/211.5 R |

*Primary Examiner*—Johnnie R. Brown
*Attorney, Agent, or Firm*—Thomas D. Kiley; Kay H. Boswell

[57] ABSTRACT

Described herein are novel 6-alkylthio and 6-arylalkylthio purine 3',5' cyclic nucleotides variously exhibiting adenyl cyclase and (in animal studies) tumor inhibitory properties, interferon potentiation, antiviral activity, and the ability to activate adenosine 3',5'-cyclic phosphate-dependent protein kinase while enjoying resistance to phosphodiesterase hydrolysis superior to that of its naturally occuring analog. The compounds are obtained by alkylation of the corresponding 6-thio nucleotide, which is in turn provided by a novel synthetic route.

7 Claims, No Drawings

6-SUBSTITUTED PURINE 3',5'-CYCLIC NUCLEOTIDES

CROSS REFERENCE TO RELATED APPLICATIONS

This is a continuation-in-part of our copending application Ser. No. 234,371, filed March 13, 1972 and now abandoned, for 6-Substituted Purine 3', 5' Cyclic Nucleotides.

BACKGROUND OF THE INVENTION

It is known that 3',5' cyclic purine ribonucleotides are produced in vivo in living animals, including man, and that cellular levels of certain ones of them such as cyclic guanosine monophosphate (C-GMP) and cyclic adenosine monophosphate (C-AMP) are regulated by specific phosphodiesterases. The biological activity of these cyclic nucleotides naturally follows from such in vivo production and regulation. Indeed, as reported in Sutherland, et al., "Cyclic Amp" *Am. Rev. Biochem.* 37, 149 (1968), cyclic AMP has now been established as an intracellular "second messenger" mediating many of the actions of a variety of different hormones.

According to the "second messenger" theory, first hormone messengers influence adenyl cyclase contained at or within cell walls to intracellularly form C-AMP from adenosine triphosphate upon receipt of the extracellular hormone signal. The formed C-AMP in turn stimulates intracellular functions particular to the target cells of the hormone. C-AMP has been shown to "activate" protein kinases which in turn occasion physiological effects such as muscle contraction, glycogenolysis, steroidogenisis and lipolysis. As a specific example of mediation of steroidogenesis by C-AMP can be mentioned cellular biosynthesis and excretion of corticosteroids as occasioned by C-AMP formed by adenyl cyclase within the cell walls of the adrenal cortex upon receipt of an extracellular signal carried by the peptide hormone ACTH.

In addition to the foregoing and as representative of the diverse roles played by C-AMP in biological processes can be mentioned implication of C-AMP as a participant in or mediator of the following metabolic reactions or pharmacologic agents: glucagon, vasopressin, lutenizing hormone, thyroid-stimulating hormone, insulin, UDPG-αtrans-glucosylase, phosphofructokinase, tryptophan pyrrolase, ketogenesis, amino acid uptake into liver proteins, acetate incorporation into fatty acids and cholesterol of liver conversion of lactate to glucose (gluconeogenesis), release of amylase, water and ion permeability, sugar transport, acid secretion in the gastric mucosa, platelet aggregation inhibition, catabolite repression, potentiation of antiviral activity of interferon, inhibition of HeLa and strain L cells in culture, and stimulation of antibody production (immunologic mechanism).

The so-called adrenergic effects of many hormones and drugs has now been attributed to the intracellular effects of cyclic AMP whose concentration is controlled by adenyl cyclase and cyclic nucleotide phosphodiesterase. Recent investigations have shown that at least part of the physiological effect of cyclic AMP is a result of the activation of specific protein kinases by cyclic AMP as, for example, in neurotubules isolated from the central nervous system.

Corollary to increasing recognition of the role played by this cyclic purine nucleotide has come the suggestion that it be administered in aid of lagging cellular processes. As one example can be mentioned the report that asthma may be caused by a genetic deficiency of adenyl cyclase. A consequence of such deficiency, of course, is a diminished capacity to intracellularly convert ATP to cyclic adenosine monophosphate.

Phosphodiesterase enzymes degrade purine nucleotides such as C-GMP and C-AMP. In the latter case the enzyme catalyzes hydrolysis of the 3',5'-cyclic adenosine monophosphate to 5'-adenosine monophosphate with consequent loss of function. A need has existed for cyclic purine nucleotide analogs which, while retaining the biological activity of the naturally occurring nucleotides, are resistant to degradation by phosphodiesterase. The availability of such C-AMP analogs, for example, could permit maintenance of desired cyclic nucleotide monophosphate levels at dosages reduced from those required with C-AMP itself. Furthermore, the differing specificity of the phosphodiesterase toward cyclic nucleotides of widely varying structure, could enhance the utility of compounds which exhibit different susceptibilities to diesterases of widely varying specificities.

The above notwithstanding, in certain cases it would appear that adenyl cyclase produces harmfully high intracellular levels of cyclic AMP. For example L.C. Chen, et al. in *The Lancet*, p. 939 (May 8, 1971) demonstrate excessive cyclic AMP production by adenyl cyclase to underly the debilitating dehydration associated with cholera. Further, there is substantial evidence that the positive inotropic and chronotropic effects of catecholamines on the heart are mediated by adenyl cyclase stimulation (S. E. Epstein et al., *Annals Int. Med.* 72:561–568, (1970 ). Hence, compounds which inhibit adenylate cyclases may act to lower heart rate and be of value in the prevention of arrythmias. The finding that the mitogen, phytohemagglutinin, stimulates the adenylates cyclase of human peripheral blood lymphocytes (J. W. Smith et al., *J. Clin. Invest.* 50:432–441, 1971) suggests that adenylate cyclase inhibitors might also be useful as immunosuppressive or anti-inflammatory agents.

From all of the foregoing, it appears that advantage would be gained by obtainment of cyclic AMP analogs equal to or superior to cyclic AMP from the standpoint of kinase activity, superior from the standpoint of resistance to phosphodiesterase, and yet capable of inhibiting adenyl cyclase activity. By such means, intracellular cyclic AMP levels could be controlled by adenyl cyclase inhibition, while overall cyclic AMP-dependent kinase activity could be controlled by regulating dosage of the said analog.

BRIEF SUMMARY OF THE INVENTION

According to this invention there are provided cyclic purine nucleotides 6-substituted with lower alkylthio or lower arylalkylthio groups, as well as ammonium and alkali metal salts thereof. These compounds are phosphodiesterase resistant compared to cyclic AMP, while equaling or improving upon its kinase activity. At the same time, the compounds display the unexpected and entirely novel property of inhibiting adenyl cyclase.

DETAILED DESCRIPTION OF THE INVENTION

The compounds of the invention are prepared by alkylation of the corresponding 6-thio compound, which may be obtained by nucleophilic attack on the 6-halo analog obtained from glycosylhydroxylblocked inosine 3', 5'-cyclic phosphate. Preferably, however, the compounds of the invention are secured according to the following synthetic route wherein "Rcp" implies 1-β-D-ribofuranosyl-3', 5'-cyclic phosphate:

washed with ethanol and ether, and dried, giving 80.4 g product suitable for further transformation. For analysis, a sample was precipitated from aqueous methanol with ether.

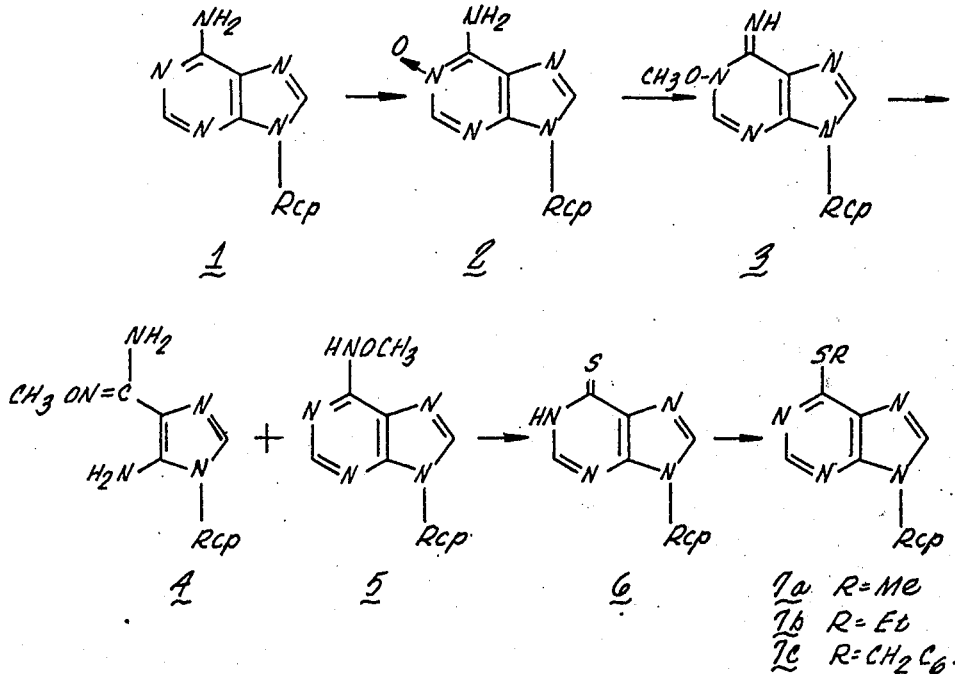

Thus, adenosine 3',5'-cyclic phosphate 1-N-oxide (2) is prepared from cyclic AMP (1) by the action of excess m-chloroperbenzoic acid in sodium acetate. Alkylation of 2 with methyl iodide, yields the corresponding $N^1$-methoxide (3). Base-catalyzed hydrolysis of (3) affords a Dimroth rearrangement product (5) as well as the novel N-methoxy imidazole cyclic phosphate (4) in ratios varying according to pH, pH 7–8 optimizing yield of (5). 9-β-D-Ribofuranosylpurin-6-thione 3',5'-cyclic phosphate (6) is obtained from 5 in large yield employing $H_2S$ under the conditions reported by Ueda et al., *Tetrahedron Letters*, 2507 (1971). From this compound, the corresponding 6-alkylated and 6-alkarylated compounds (7) may be obtained in large yield by alkylation with appropriate halides under basic conditions. Thus, methyl iodide affords 7a, ethyl iodide 7b and benzyl bromide 7c. Preferably R is lower alkyl (eg. $C_1$–$C_8$), most preferably linear or branched $C_1$–$C_4$. Alternatively, R may be lower alkaryl, eg. linear or branched ($C_1$–$C_8$) phenyl, preferably ($C_1$–$C_4$) phenyl.

The invention is further described and illustrated in the examples of the preferred embodiments which follow.

EXAMPLE 1

$N^1$-Methoxyadenosine 3',5'-cyclic phosphate

Adenosine 3', 5'-cyclic phosphate $N^1$-oxide (76.0 g, 0.200 mole as the dihydrate) was dissolved in a solution of 400 ml DMSO and 31 g (0.204 mole) 1,5-diazabicyclo[5.4.0]undec-5-ene. The solution was cooled to 15°, and 40 ml methyl iodide was added with stirring at ambient temp. After 30 min the mixture had gelled; 1.5 l ethanol was added and the solid was thoroughly homogenized by vigorous stirring. The solid was filtered, and the resulting paste was resuspended in 2 l ethanol and homogenized. The product was again filtered, Anal. Calcd for $C_{11}H_{14}N_5O_7P.\frac{1}{2}$ $H_2O$: C, 35.88; H, 4.11; N, 19.02%. Found: C 35.88; H, 4.46; N, 18.69%.

EXAMPLE 2

5-Amino-N'-methoxy-1-β-D-ribofuranosyl-imidazol-4-carboxamidine 3', 5'-cyclic phosphate (product A) and 6-methoxyamino-9-β-D-ribofuranosylpurine 3',5'-cyclic phosphate (product B).

A solution of 30 g $N^1$-methoxyadenosine 3',5'-cyclic phosphate (81.5 mmole), 20 g $NaHCO_3$ (238 mmole), and 300 ml $H_2O$ was refluxed 45 min. The pH of the solution was adjusted to 2.5 with Dowex 50×8($H^+$) while warm, and a water pump vacuum was applied to the mixture to remove $CO_2$. The pH was readjusted to 9–10 with NaOH, and the resin was removed by filtration. The solution was passed onto a column contianing 400 ml Dowex 1×2 (formate, 100–200 mesh), and the column was washed well with water. The column was eluted with a gradient of 4 liters water in the mixing chamber and 4 liters 4N formic acid in the reservoir. The first major product, coming after about 2 liters of eluate, was product A, giving 5.4 g (19%) after evaporation of the solvent and trituration of the residue with ethanol. A sample was recrystallized from water for analysis.

Anal. Calcd for $C_{10}H_{16}N_5O_7P$: C, 34.39; H, 4.62; N, 20.05%. Found: C, 34.54; H, 4.70; N, 19.96% .

After approximately 6 liters of eluate, another product began to appear. Evaporation of the appropriate fractions and precipitation of the product from aqueous methanol with ether gave 14.6 g product B (49%).

Anal. Calcd for $C_{11}H_{14}N_5O_7P.\frac{1}{2}$ $H_2O$: C, 35.88; H, 4.11; N, 19.02%. Found: C, 35.64; H, 4.09; N, 18.71.

EXAMPLE 3

9-β-D-Ribofuranosylpurin-6-thione 3', 5'-cyclic phosphate

Hydrogen sulfide gas was conducted into 25 ml pyridine (temp <−60°) until the volume of solution was 75 ml. This solution was added to a frozen solution of 12.0 g (33 mmoles) 6-methoxyamino-9-β-D-ribofuranosylpurine 3', 5'-cyclic phosphate and 25 ml water in a steel bomb. The bomb was sealed and kept at 60° for 48 hr. The bomb was cooled, opened and allowed to stand while H$_2$S evaporated. The resulting mixture was diluted with 100 ml water, filtered, and applied to a column containing 1000 ml Dowex 50×8 (H$^+$) 100–200 mesh, and the column was eluted with water. Fractions of 24 ml were collected, and 6.30 g product crystallized from the fraction tubes. Evaporation of the fractions still containing product gave 3.45 g additional product; the total yield was 9.75 g (82%).

Anal. Calcd for C$_{10}$H$_{11}$N$_4$O$_6$PS H$_2$O: C, 32.97; H, 3.60; N, 15.38%. Found: C, 33.02; H, 3.40; N, 15.40%.

EXAMPLE 4

6-Methylthio-9-β-D-ribofuranosylpurine 3', 5'-cyclic phosphate

A solution of 9.1 g (25 mmole) of 9-β-D-ribofuranosylpurin-6-thione 3', 5'-cyclic phosphate hydrate and 6.2 g (50 mmole) sodium carbonate hydrate in 25 ml H$_2$O was diluted with 100 ml methanol and 15 ml methyl iodide. The mixture was stirred 1 hr and evaporated to a small volume, then applied to a column containing 800 ml Dowex 50×8 (H$^+$form, 100–200 mesh). The column was eluted with water and 23 ml fractions were collected. Impurities were eluted first, and fractions containing pure product were evaporated in vacuo to dryness. The residue was taken up on methanol. Addition of ether gave a white solid which was collected on a filter and dried; yield 8.08 g (85%). A sample was recrystallized from ethanol-water for analysis.

Anal. Calcd for C$_{11}$H$_{13}$N$_4$O$_6$PS. 1¼ H$_2$O: C, 34.51; H, 4.08; N, 14.64%. Found: C, 34.40; H, 3.66; N, 14.53%.

EXAMPLE 5

6-Ethylthio-9-β-D-ribofuranosylpurine 3', 5'-cyclic phosphate

A solution of 6.0 g (16.5 mmole) 9-β-D-ribofuranosylpurin-6-thione 3', 5'-cyclic phosphate and 3.7 g (33 mmole) sodium carbonate hydrate in 25 ml water was diluted with 100 ml methanol and 10 ml ethyl iodide. After 10 min stirring, the pH of the mixture was adjusted to 1.0 with Dowex 50×8 (H$^+$), then back to 7.0 with NaOH. The resin was filtered and the filtrate was applied to a 2.5×20 cm column of Dowex 1×2 (formate form, 100–200 mesh). After washing well with water, the product was eluted with 2N ammonium formate and 23 ml fractions were collected. The fractions containing product were passed through a column of 1000 ml Dowex 50×8 (H$^+$form, 100–200 mesh). Solvent was removed in vacuo, the residue was taken up in MeOH, and the product was precipitated by addition of ether. The product was collected on a filter and dried; yield 3.1 g (50%).

Anal. Calcd for C$_{12}$H$_{15}$N$_4$O$_6$PS: C, 38.50; H, 4.04; N, 14.97% Found: C, 38.22; H, 4.46; N, 14.60%.

EXAMPLE 6

6-Benzylthio-9-β-D-ribofuranosylpurine 3', 5'-cyclic phosphate.

A solution of 4.82 g (13.2 mmole) 9-β-D-ribofuranosylpurin-6-thione 3', 5'-cyclic phosphate and 3.28 g sodium carbonate hydrate in 20 ml water was diluted with 80 ml methanol and 1.9 ml (16 mmole) benzyl bromide. The mixture was stirred 1 hr, then 3 ml formic acid was added. The methanol was removed in vacuo, 150 ml water was added, and the solution was extracted with 100 ml ether. The aqueous phase was applied to the top of a column containing 1000 ml Dowex 50×8 (H$^+$form, 100–200 mesh). The column was eluted with 1000 ml water, and 23 ml fractions were collected. The product began to appear after 600 ml of eluate. Elution of the column with 1000 ml 50% aqueous ethanol brought off the rest of the product. The fractions containing product were pooled and evaporated in vacuo. Addition of hot ethyl acetate induced crystallization of the residue, which was then filtered and dried; yield, 4.52 g (75%).

anal. Calcd for C$_{17}$H$_{17}$N$_4$O$_6$PS.H$_2$O; C, 44.93; H, 4.22; N, 12.33%. Found: C, 44.88; H, 4.16; N, 11.97%.

Table I

| ULTRAVIOLET SPECTRA OF THE NUCLEOTIDES | | |
|---|---|---|
| | pH | $\lambda_{max}$ (nm) | $\epsilon \times 10^{-3}$ |
| N$^1$-Methoxyadenosine 3',5'-cyclic phosphate | 1 | 257 | 12.4 |
| | 11 | 257 | 12.5 |
| | | 285 (sh) | 3.54 |
| 6-Methoxyamino-9-β-D-ribofuranosylpurine 3',5'-cyclic phosphate | 1 | 264 | 15.0 |
| | H$_2$O | 266 | 13.9 |
| | 11 | 268 | 11.75 |
| 5-Amino-N'-methoxy-9-β-D-ribofuranosylimidazol-4-carboxamidine 3',5'-cyclic phosphate | 1 | 281 | 9.63 |
| | H$_2$O | 258 | 9.49 |
| | 11 | 257 | 10.2 |
| 9-β-D-Ribofuranosylpurin-6-thione 3',5'-cyclic phosphate | 1 | 321 | 23.7 |
| | 11 | 310 | 22.2 |
| 6-Methylthio-9-β-D-ribofuranosylpurine 3',5'-cyclic phosphate | 1 | 292 | 16.4 |
| | 11 | 288 | 18.0 |
| 6-Ethylthio-9-β-D-ribofuranosylpurine 3',5'-cyclic phosphate | 1 | 293 | 16.3 |
| | 11 | 290 | 18.4 |
| 6-Benzylthio-9-β-D-ribofuranosylpurine 3',5'-cyclic phosphate | 1 | 292 | 17.0 |
| | 11 | 291 | 18.3 |

EXAMPLE 7

ASSAY FOR ADENYL CYCLASE ACTIVITY

Lunt alveolar tissue was obtained from normal guinea pigs. The tissue was minced and a Duall tissue grinder was used to prepare a 20% homogenate in chilled buffer containing 1 mM MgCl$_2$ and 2 mM glycylglycine, pH 7.5 (F. Murad et al., *J. Biol. Chem.* 237: 1233, 1962). The homogenate was strained through four layers of gauze and centrifuged at 1000xg for 15 min at 4°. The pellet was resuspended in the original volume of buffer and recentrifuged. The pellet was again resuspended in buffer and 0.5 – 1.0 ml aliquots were sealed in ampoules and stored under liquid nitrogen for future assay of adenylate cyclase activity. Samples stored in this manner exhibited undiminished activity for as long as 3 months. Protein was determined by the method of Lowry et al., *J. Biol. Chem.* 193: 265, 1951, with crystalline bovine serum albumin as standard.

Adenylate cyclase activity was assayed in duplicate by a modification of previously published methods (G. Krishna et al., *J. Pharmacol. Exp. Therap.* 163: 379, 1968; G. S. Levey and S. E. Epstein, *Circ. Res.* 24: 151, 1969). The total assay volume was 0.59 ml and contained 1.8 mM $MgCl_2$, 0.8 mM glycylglycine, 32 mM Tris (pH 7.8), 1.2 mM ATP, $3-5\times10^6$ cpm [$\alpha$-$^{32}$P] ATP, and particulate enzyme fraction (100–150 µg. lung protein). Concentrated solutions of compounds to be tested were prepared fresh daily by dissolution in water, ethanol, or dimethyl sulfoxide; 5–10 µl of the solution was added to the incubation mixture to give the desired final concentration. Control assays (without compound) contained solvent alone.

The incubation mixture was reacted for 15 min at 37° in a shaker, and then boiled for 3 min to inactivate the cyclase. One hundred µl of a solution containing 4 µmoles ATP, 1.25 µmoles cyclic AMP, and 0.15µCi [$^3$H] cyclic AMP was added to the reaction mixture. The denatured enzyme was sedimented by centrifugation and the supernatant applied to a Dowex 50W-X8 (100–200 mesh) column of approximately 1 cm$^3$ bed volume. The column was eluted with water and the first 3 ml collected were discarded except for the blank (no enzyme) assays, for which this fraction provided an accurate measure of the (radio-active) ATP added. The next 4 ml eluted contained 55–70% of the total cyclic AMP present. This fraction was treated with 0.5 ml of 0.18 M $ZnSO_4$ followed by 0.5 ml of an equivalent $Ba(OH)_2$ solution. The resulting precipitate was spun down and the $ZnSO_4$-Ba(OH)$_2$ treatment repeated without disturbing the first precipitate. After centrifugation, 1 ml of supernatant containing [$^{32}$P] cyclic AMP and [$^3$H] cyclic AMP was mixed with 15 ml of scintillator (100 g naphthalene, 14 g PPO, and 0.1 g dimethyl POPOP per 2 l dioxane) and counted. The amount of [$^{32}$P] cyclic AMP formed in each assay was corrected for recovery losses subsequent to the incubation with the aid of the [$^3$H] cyclic AMP found in each case. Activities are reported in Table II as I/50 values, ie, concentration required for 50% enzyme inhibition.

TABLE II

| ADENYL CYCLASE INHIBITION | |
|---|---|
| Compound | $I_{50}$ (mM) |
| 6-Methylthio-9-($\beta$-D-ribofuranosyl)purine 3',5'-cyclic phosphate | 0.34 |
| 6-Ethylthio-9-($\beta$-D-ribofuranosyl)purine 3',5'-cyclic phosphate | 1.0 |
| 6-Benzylthio-9-($\beta$-D-ribofuranosyl)purine 3',5'-cyclic phosphate | 7.0 |

EXAMPLE 8

RESISTANCE TO PHOSPHODIESTERASE (PDE) DEGRADATION

The cyclic AMP phosphodiesterases used were ammonium sulfate precipitates of 100,000× g supernatants prepared from tissue homogenates of rabbit kidney. The ability of the analogs to serve as substrates for the cAMP phosphodiesterase was measured by the previously described method of Muneyama et al., *Biochem.* 10, 2390 (1971). Inorganic phosphate, released from the 5'-monophosphate formed upon treatment of the analog with PDE was determined colorimetrically. The inorganic phosphate release was effected with snake venom 5'-nucleotidase of *e coli* alkaline phosphatase. The basic mixture contained the following (amounts in µmoles): Tris buffer, pH 7.5, 40; magnesium acetate, 25; cAMP or analog, 0.1; enzyme, 100–500 µg in a final volume of 1.0 ml. One unit of activity was defined as that amount of enzyme catalyzing the hydrolysis of 1.0 µmole in 10 minutes at 37°C. Table III reports rates of analog hydrolysis relative to cyclic AMP ($\alpha$).

TABLE III

| RESISTANCE TO PDE HYDROLYSIS | |
|---|---|
| Compound | ($\alpha$) |
| 6 | 1.06 |
| 7a | 0.41 |
| 7b | 0.57 |
| 7c | 0.54 |

EXAMPLE 9

ACTIVATION OF BOVINE BRAIN PROTEIN KINASE

Cyclic AMP-dependent protein kinase was purified to the stage of DEAE cellulose chromatography from bovine brain using the procedure of Miyamoto et al., *J. Biol. Chem.* 244, 6395 (1969). Protein kinase activity was assayed by measuring the incorporation of $^{32}$P-phosphate into histone from $\gamma$-$^{32}$P labeled ATP. The incubation mixture contained (amounts in µmoles): sodium glycerol phosphate buffer, pH 6, 10; $\gamma$-$^{32}$P-ATP, ~2 × 10$^6$ cpm, 0.001; magnesium acetate, 2; sodium fluoride, 2; EDTA, 0.06; histone, 40 – 400 µg; cAMP, cGMP or analog as indicated; purified protein kinase, 5 – 25 µg in a final volume of 0.2 ml. Activation constants (Ka) were determined according to the procedure of Muneyama et al., supra. The Ka values relative to cyclic AMP (Ka') are reported in Table IV and compared to Ka' for compound 6.

TABLE IV

| ACTIVATION OF BOVINE BRAIN KINASE | |
|---|---|
| Compound | Ka' |
| 6 | 0.56 |
| 7a | 1.45 |
| 7b | 2.0 |
| 7c | 1.25 |
| Ka' = Ka, cyclic AMP/Ka analog | |

From Examples 8 and 9 it will be seen that the preferred compounds of the invention are superior in phosphodiesterase resistance and cyclic AMP-dependent kinase activation not only to cyclic AMP but also to their known precursor (6).

Tested according to the virus rating (VR) method of Sidwell et al., *Proc. Soc. Exp. Biol. Med.* 131, 1223

(1969) compound 7a exhibited activity as against Herpes viruses (Types 1 and 2), 7b against Herpes Type 1 and Rhino viruses, and 7c in respect to Herpes Type 2 virus. Moreover, compound 7c, when injected intraperitoneally (83 μmoles/Kg) into mice, inhibited growth of surgically implainted 6-methylthio-purine riboside-resistant Ehrlich carcinomas.

Tested in vitro with L-929 cells, the 6-alkylthio compounds (ie, compounds 7a and 7b exhibited marked interferon potentiation, whereas the corresponding 6-thio compound (6) did not.

In light of the foregoing explication of the preferred embodiments of the invention, variations within the spirit and scope thereof will be apparent to those skilled in the art. For example, the cyclic nucleotides of the invention may be employed in the form of their physiologically acceptable salts, eg, ammonium, alkali metal and alkyl amine salts, obtained by neutralization of the free nucleotide with base appropriate to the desired end. The O-acylated (eg, $C_1$–$C_{18}$ acyl) analogs may be secured by reaction of the free nucleotides or salts thereof with corresponding acid anhydrides or acyl halides (eg, acetyl, butyryl, hexanoyl, octanoyl, lauryl, adamantoyl, etc.) in base. Sutherland et al., *Biochim. et Biophys. Acta* 148, 106 (1967) have demonstrated that acylation of C-AMP enhances cellular transport of purine nucleotides.

We claim:

1. A compound of structure:

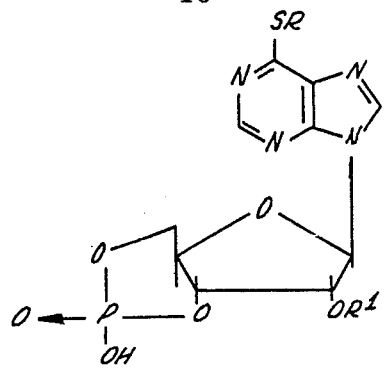

wherein R is $C_1C_8$ alkyl or $C_1$–$C_8$ alkylphenyl and $R^1$ is hydrogen or $C_1$ – $C_{18}$ acyl.

2. An ammonium or alkali metal salt of a compound according to claim 1.

3. A compound according to claim 1 wherein $R^1$ is hydrogen.

4. A compound according to claim 3 wherein R is methyl.

5. A compound according to claim 3 wherein R is ethyl.

6. A compound according to claim 3 wherein R is benzyl.

7. A compound according to claim 1 wherein $R^1$ is acetyl.

* * * * *